(12) United States Patent
Cawley et al.

(10) Patent No.: US 9,636,121 B2
(45) Date of Patent: May 2, 2017

(54) FACET DISTRACTION DEVICE, FACET JOINT IMPLANT, AND ASSOCIATED METHODS

(75) Inventors: Trace Cawley, Boca Raton, FL (US); Peter Harris, Boca Raton, FL (US); Doris Blake, DeLay Beach, FL (US)

(73) Assignee: HARBINGER MEDICAL GROUP, LLC, Lafayette, LA (US)

(*) Notice: Subject to any disclaimer, the term of this patent is extended or adjusted under 35 U.S.C. 154(b) by 775 days.

(21) Appl. No.: 12/616,435

(22) Filed: Nov. 11, 2009

(65) Prior Publication Data
US 2010/0137910 A1    Jun. 3, 2010

Related U.S. Application Data

(60) Provisional application No. 61/113,261, filed on Nov. 11, 2008.

(51) Int. Cl.
| A61B 17/70 | (2006.01) |
| A61B 17/16 | (2006.01) |
| A61B 17/17 | (2006.01) |
| A61B 17/02 | (2006.01) |
| A61B 17/32 | (2006.01) |

(52) U.S. Cl.
CPC ...... *A61B 17/1671* (2013.01); *A61B 17/1757* (2013.01); *A61B 17/1659* (2013.01); *A61B 17/7064* (2013.01); *A61B 2017/0256* (2013.01); *A61B 2017/320044* (2013.01)

(58) Field of Classification Search
CPC A61F 2/4405; A61B 17/7064; A61B 17/7062
USPC .............. 606/246–279; 623/17.11–17.16
See application file for complete search history.

(56) References Cited

U.S. PATENT DOCUMENTS

| 5,609,636 | A  | * | 3/1997  | Kohrs et al. ............. 623/17.16 |
| 6,371,988 | B1 | * | 4/2002  | Pafford et al. ........... 623/17.11 |
| 6,706,067 | B2 | * | 3/2004  | Shimp ................. A61F 2/4455 623/17.11 |
| 2001/0016775 | A1 | * | 8/2001  | Scarborough et al. .... 623/17.16 |
| 2001/0020186 | A1 | * | 9/2001  | Boyce et al. ............ 623/17.16 |
| 2002/0193881 | A1 | * | 12/2002 | Shapiro et al. .......... 623/17.11 |
| 2003/0036798 | A1 | * | 2/2003  | Alfaro et al. ............ 623/17.16 |
| 2004/0167520 | A1 | * | 8/2004  | Zucherman et al. ......... 606/61 |
| 2005/0149192 | A1 | * | 7/2005  | Zucherman et al. ..... 623/17.11 |
| 2007/0016195 | A1 | * | 1/2007  | Winslow et al. ........... 606/61 |
| 2007/0027546 | A1 | * | 2/2007  | Palm et al. ............. 623/17.16 |
| 2007/0055373 | A1 | * | 3/2007  | Hudgins et al. ......... 623/17.11 |
| 2008/0154374 | A1 | * | 6/2008  | Labrom ................. 623/17.12 |
| 2009/0036927 | A1 | * | 2/2009  | Vestgaarden .............. 606/247 |
| 2009/0076551 | A1 | * | 3/2009  | Petersen ................. 606/247 |

* cited by examiner

*Primary Examiner* — Eduardo C Robert
*Assistant Examiner* — Atiya Mahmud
(74) *Attorney, Agent, or Firm* — Phillips Ryther & Winchester; Matthew D. Thayne

(57) ABSTRACT

In various exemplary embodiments, the present invention provides devices, implants, and methods for distracting and/or stabilizing a facet joint of the spine of a patient or other similar joint or bony structures, optionally including modifying the facet joint and implanting an implant in the facet joint so as to distract the foramen in order to reduce compression on nerve roots.

12 Claims, 18 Drawing Sheets

FACET DISTRACTION DEVICE, FACET JOINT IMPLANT, AND ASSOCIATED METHODS

CROSS-REFERENCE TO RELATED APPLICATION

The present non-provisional patent application/patent claims the benefit of priority of U.S. Provisional Patent Application No. 61/113,261, filed on Nov. 11, 2008, and entitled "FACET DISTRACTION DEVICE AND ASSOCIATED METHODS," the contents of which are incorporated in full by reference herein.

FIELD OF THE INVENTION

The present invention relates generally to devices, implants, and methods for performing surgical procedures, especially spinal surgical procedures. More specifically, the present invention relates to devices, implants, and methods for distracting and/or stabilizing a facet joint of the spine of a patient or other similar joint or bony structures, optionally including modifying the facet joint and implanting an implant in the facet joint so as to distract the foramen in order to reduce compression on nerve roots.

BACKGROUND OF THE INVENTION

Facet joints are in almost constant motion with the spine and quite commonly wear out and/or become degenerated. When facet joints become worn and/or degenerated, the cartilage may become thin or disappear and there may be a reaction of the bone of the joint underneath, producing an overgrowth of bone spurs and an enlargement of the joint. The facet joint is then said to have arthritic (literally, joint inflammation-degeneration) changes, or osteoarthritis, that may produce considerable back pain with continued motion. This condition may also be referred to as "facet joint disease" or "facet joint syndrome."

Facet joint disorders are some of the most common of all of the recurrent, disabling lower back and neck problems, and may cause serious symptoms and disability for patients. Degeneration of the adjoining disc is almost always present, so the segment often requires a bone fusion. Typically, the adjacent vertebrae are immobilized using a cage or the like while an associated bone graft is allowed to "take," for example, using a conventional pedicle screw system, a plate system, or the like. Such a pedicle screw system typically consists of a plurality of pedicle screws that are anchored to adjacent levels of the spine and connected with stabilizing rods or the like. Such a plate system typically consists of a plate that is anchored to adjacent levels of the spine and, optionally, connected to the implantable device and bone graft.

Another attractive option when treating various spinal diseases, injuries, and conditions is to immobilize the associated facet joint(s) using one or more facet bolts, clips, or the like. In order to accomplish this, the superior and inferior facets to be joined must be distracted and securely held during drilling and bolt placement, for example. It is also desirable that they are compressed either before or during drilling and bolt placement. This can be a tricky process, which is never desirable during a surgical procedure.

Thus, what are needed in the art are simplified devices, implants, and methods for distracting and securely holding superior and inferior facets to be joined (simultaneously compressing the associated facet joint), drilling the hole through which a facet fixation device will be placed, and placing the facet fixation device to a desired penetration depth. Such devices, implants, and methods are provided by the present invention. Advantageously, the facet fixation devices of the present invention may be used to distract the foramen in order to reduce compression on nerve roots.

BRIEF SUMMARY OF THE INVENTION

In various exemplary embodiments, the present invention provides devices, implants, and methods for distracting and/or stabilizing a facet joint of the spine of a patient or other similar joint or bony structures, optionally including modifying the facet joint and implanting an implant in the facet joint so as to distract the foramen in order to reduce compression on nerve roots.

In one exemplary embodiment, the present invention provides a facet distraction instrument, including: a first member configured and sized to engage a first facet of a facet joint; a second member configured and sized to engage a second facet of the facet joint, wherein the second member is offset from the first member; and an actuation mechanism coupled to the first member and the second member, wherein the actuation mechanism is operable for moving the first and second members relative to one another, thereby distracting the first facet relative to the second facet. Optionally, the first and second members each include a substantially arc shaped member. Optionally, the actuation mechanism includes first and second handles hingedly connected to the first and second members. In this exemplary embodiment, the facet distraction instrument also includes a drill member disposed along a centerline of the facet distraction instrument between the first and second members, wherein the drill member is operable for removing bone material from the facet joint subsequent to distraction of the first and second facets.

In another exemplary embodiment, the present invention provides a facet joint stabilization device, including: a body section; a first lobe section protruding outwardly from the body section; and a second lobe section protruding outwardly from the body section. Optionally, the body section has a substantially rectangular shape, and each of the first lobe section and the second lobe section has a substantially semicircular shape. The facet joint stabilization device is a one of a prismatic structure and a tapering structure. In one exemplary embodiment, the first lobe section and the second lobe section are in alignment with respect to one another in relation to the body section. In another exemplary embodiment the first lobe section and the second lobe section are offset with respect to one another in relation to the body section. Optionally, one or more of the body section, the first lobe section, and the second lobe section include one or more friction structures on an outer surface thereof. Optionally, one or more of the body section, the first lobe section, and the second lobe section include a relatively compressible outer material and a relatively rigid inner material. Preferably, a portion of the relatively rigid inner material protrudes through and beyond a surface of the relatively compressible outer material when the relatively compressible outer material is compressed in a facet joint space. Optionally, the facet joint stabilization device includes one or more bone materials.

In a further exemplary embodiment, the present invention provides a facet joint stabilization method, including: disposing a facet joint stabilization device in a recess formed in a facet joint of a spine of a patient, the facet joint stabilization device comprising: a body section; a first lobe section protruding outwardly from the body section; and a second lobe section protruding outwardly from the body section. Optionally, the body section has a substantially rectangular shape, and each of the first lobe section and the second lobe section has a substantially semicircular shape. The facet joint stabilization device is a one of a prismatic structure and a tapering structure. In one exemplary embodiment, the first lobe section and the second lobe section are in alignment with respect to one another in relation to the body section. In another exemplary embodiment the first lobe section and the second lobe section are offset with respect to one another in relation to the body section. Optionally, one or more of the body section, the first lobe section, and the second lobe section include one or more friction structures on an outer surface thereof. Optionally, one or more of the body section, the first lobe section, and the second lobe section include a relatively compressible outer material and a relatively rigid inner material. Preferably, a portion of the relatively rigid inner material protrudes through and beyond a surface of the relatively compressible outer material when the relatively compressible outer material is compressed in a facet joint space. Optionally, the facet joint stabilization device includes one or more bone materials. Optionally, the method also includes distracting the facet joint prior to disposing the facet joint stabilization device in the recess formed in the facet joint of the spine of the patient.

BRIEF DESCRIPTION OF THE DRAWINGS

The present invention is illustrated and described herein with reference to the various drawings, in which like reference numbers are used to denote like device/implant components and/or method steps, as appropriate, and in which.

DETAILED DESCRIPTION OF THE INVENTION

In various exemplary embodiments, the present invention provides novel devices, implants, and methods for distracting and stabilizing a superior facet and an inferior facet of a facet joint to be immobilized during an interbody fusion or other spinal immobilization procedure (simultaneously compressing the associated facet joint, distracting the foramen to reduce compression on nerve roots, etc.). The present invention may include drilling a hole or bore through which a facet stabilization device is placed, optionally after joint distraction, and placing the facet stabilization device to a desired penetration depth in the hole or bore. In various exemplary embodiments, the present invention also provides novel facet stabilization devices.

Figure 1:
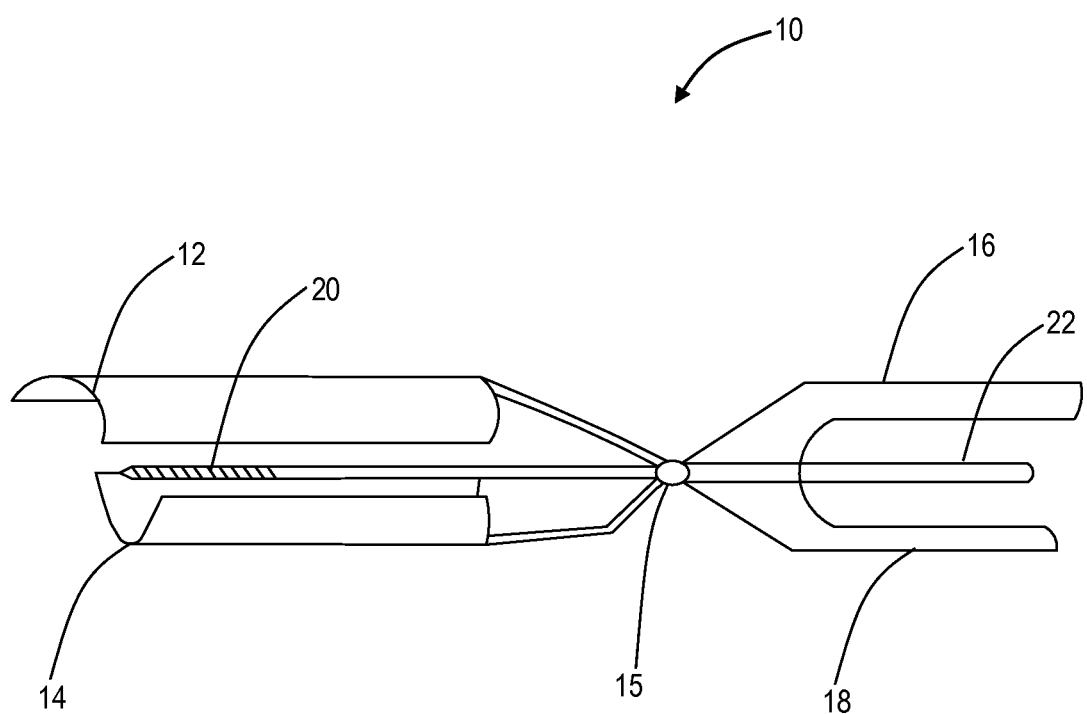
FIG. 1 is a perspective diagram illustrating one exemplary embodiment of the facet distraction instrument of the present invention.

Referring to FIG. 1, a facet distraction instrument 10 is illustrated according to an exemplary embodiment of the present invention. The facet distraction instrument 10 includes a first arc shaped member 12 and a second arc shaped member 14. The first arc shaped member 12 and the second arc shaped member 14 may have any suitable shape for securely engaging the facets of the spine of a patient. The arc shaped members 12,14 are offset from each other and share a common plane through a center axis 15 of the facet distraction instrument 10. The facet distraction instrument 10 also includes a first handle portion 16 and a second handle portion 18. The first handle portion 16 is operably connected to the second arc shaped member 14 and the second handle portion 18 is operably connected to the first arc shaped member 12. When force is exerted on the two handle portions 16,18, the force is translated to the two arc shaped members 12,14, causing them each to cross the center axis 15 of the facet distraction instrument 10. Thus, the two handle portions 16,18 may be squeezed, thereby actuating the two arc shaped members 12,14, which are displaced towards and past each other, thereby distracting the facets with which they are engaged.

The facet distraction instrument 10 may further include a cannulated drill portion 20 or the like. For example, the cannulated drill portion 20 may extend through and in plane with the center axis 15 of the facet distraction instrument 10 and between the two handle portions 16,18 and between the two arc shaped members 12,14. The cannulated drill portion 20 is operable to receive a drill bit or the like at an opening 22. For example, the drill bit may be inserted once the facet joint is in a desired position (i.e. at a desired degree of distraction). The drill bit is inserted through the opening 22, extending through the cannulated drill portion 20 to the facet joint.

Figure 2:
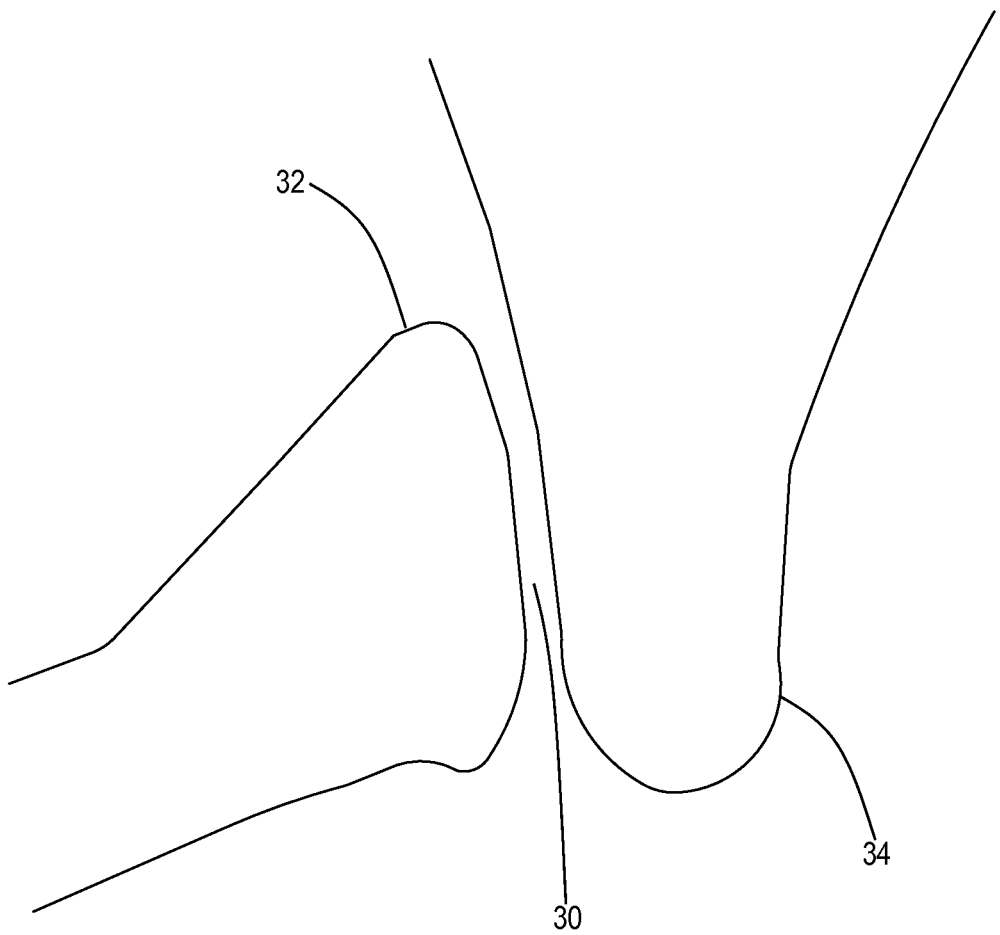
FIG. 2 is a representative view of a facet joint of the spine of a patient.
Figure 3:
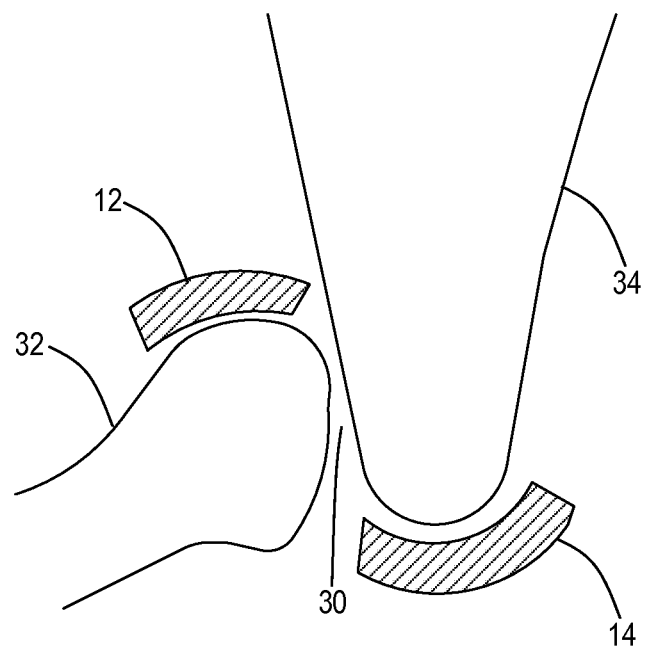
FIG. 3 is a representative view of the facet joint of the spine of the patient, highlighting the placement of the facet distraction instrument of FIG. 1.
Figure 4:
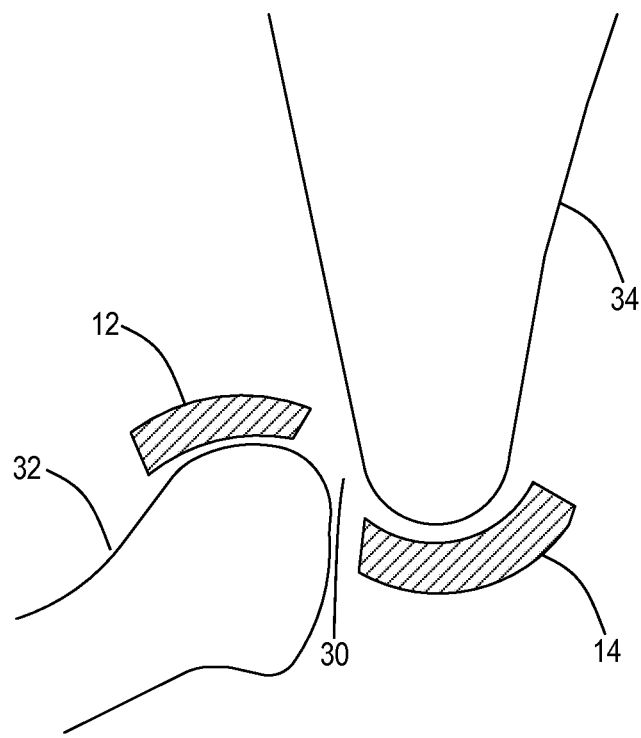
FIG. 4 is a representative view of the facet joint of the spine of the patient, highlighting the actuation of the facet distraction instrument of FIG. 1.
Figure 5:
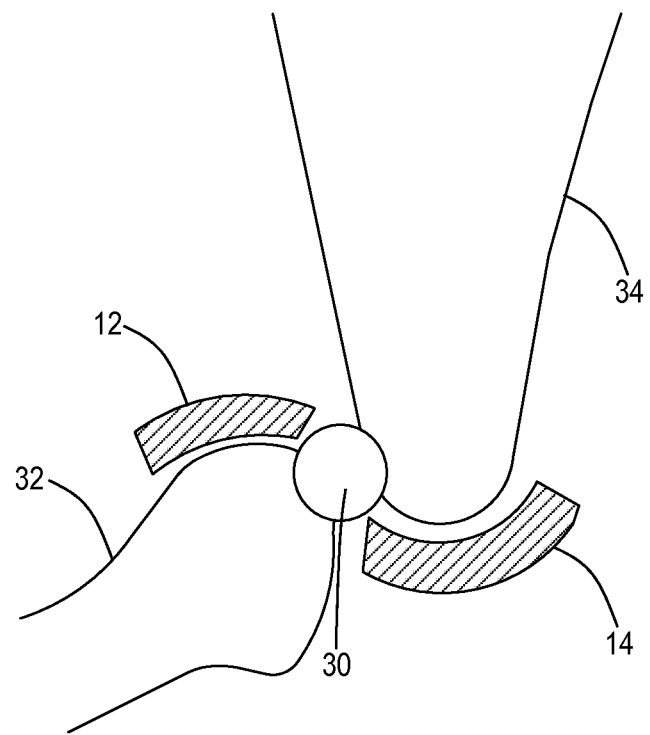
FIG. 5 is a representative view of the facet joint of the spine of the patient, highlighting the actuation of the facet distraction instrument of FIG. 1 and the placement area for a facet stabilization device.

Referring to FIGS. 2-4, a representative view of a facet joint is illustrated according to an exemplary embodiment of the present invention. FIG. 2 illustrates a facet joint 30 that is formed at the intersection of an inferior facet 32 and a superior facet 34. Referring specifically to FIG. 3, the first arc shaped member 12 of the facet distraction instrument 10 is engaged with the inferior facet 32 and the second arc shaped member 14 is engaged with the superior facet 34. FIG. 3 illustrates an initial position where a surgeon has positioned the facet distraction instrument 10 within a patient to engage the facets 32,34. The two arc shaped members 12,14 are positioned to substantially immobilize the two facets 32,34 before and during the distraction process. Referring specifically to FIG. 4, once the two arc shaped members 12,14 are engaged with the two facets 32,34, then the two handle portions 16,18 are squeezed together to exert a force on the two arc shaped members 12,14, which translates to the facets 32,34, thereby distracting them relative to each other. The inferior facet 32 is shown being pushed by the first arc shaped member 12 in an opposite direction than the superior facet 34, which is being pushed by the second arc shaped member 14. Referring specifically to FIG. 5, the facet joint 30 is held in the distracted configuration. Here, the facets 32,34 are held in a desired position based on the degree of deployment of the facet distraction instrument 10. In this configuration, the cannulated drill portion 20 may be used to drill through the facet joint 30, producing a hole or bore. It will be readily apparent to those of ordinary skill in the art that other shaped/sized recesses may also be formed in the facets 32,34 using the cannulated drill portion 20 or another shaping tool associated with the facet distraction instrument 10, such that a variety of stabilizing implants may be subsequently placed. Once the hole or bore is drilled (or other shaped recess is formed), a plug or other implant device may be inserted to facilitate stabilization. Optionally, the plug or other implant device may be inserted through the cannulated drill portion 20 or the like. These implant devices are described in greater detail herein below.

A variety of other instruments may be used in conjunction with, as a compliment to, or in place of the facet distraction instrument 10 (FIG. 1) described above.

Figure 6:
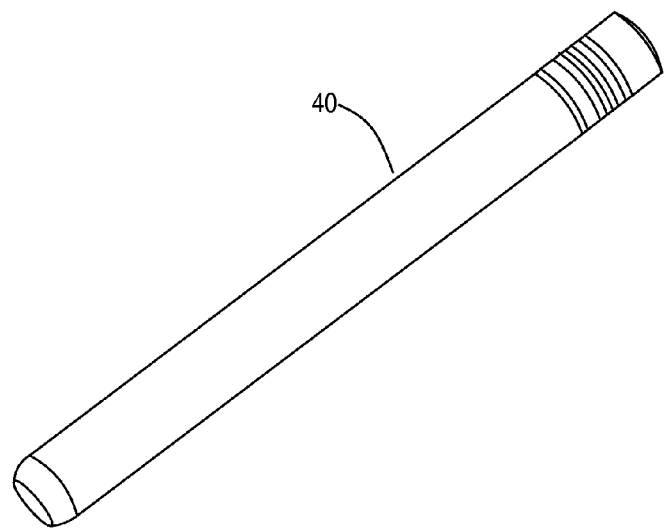
FIG. 6 is a perspective diagram illustrating one exemplary embodiment of a dilator tube of the present invention, used in conjunction with the facet stabilization device of the present invention.
Figure 7:
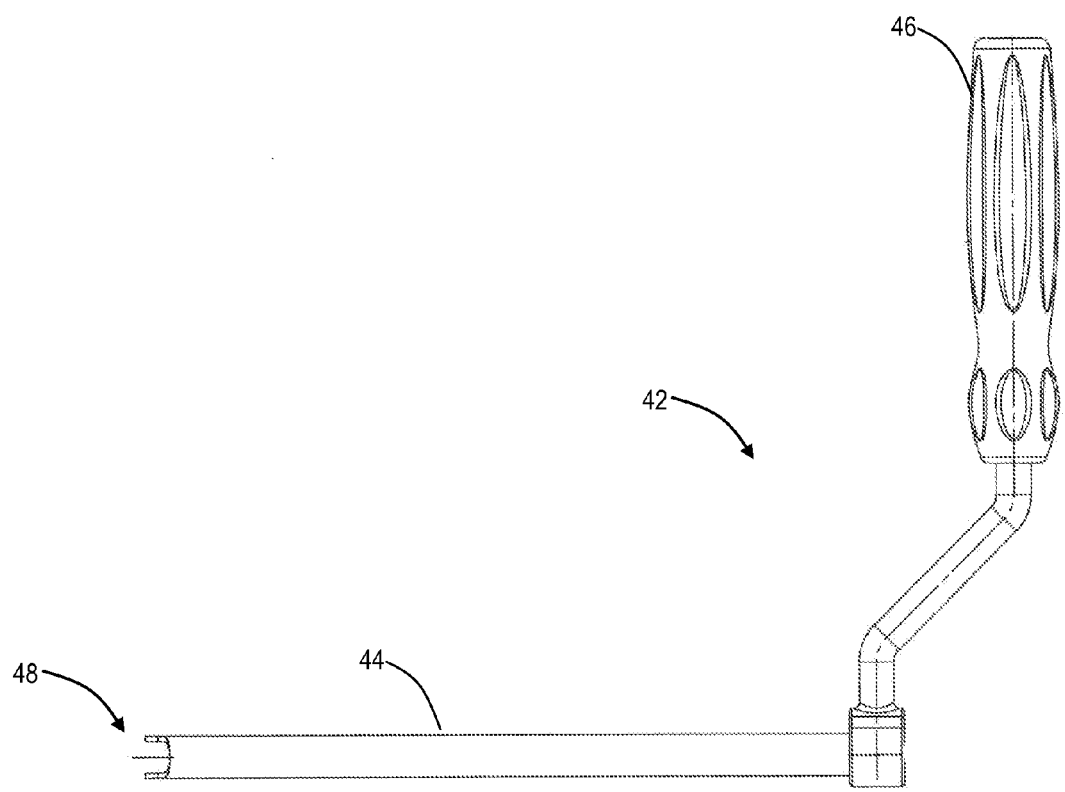
FIG. 7 is a planar diagram illustrating one exemplary embodiment of a drill guide assembly of the present invention, used in conjunction with the facet stabilization device of the present invention.
Figure 8:
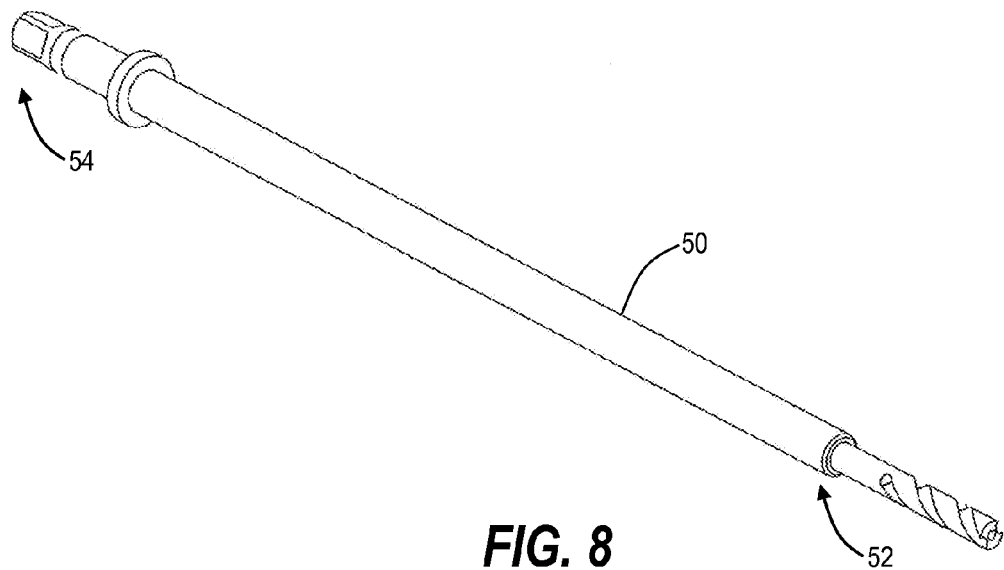
FIG. 8 is a perspective diagram illustrating one exemplary embodiment of a drill assembly of the present invention, used in conjunction with the facet stabilization device of the present invention.
Figure 9:
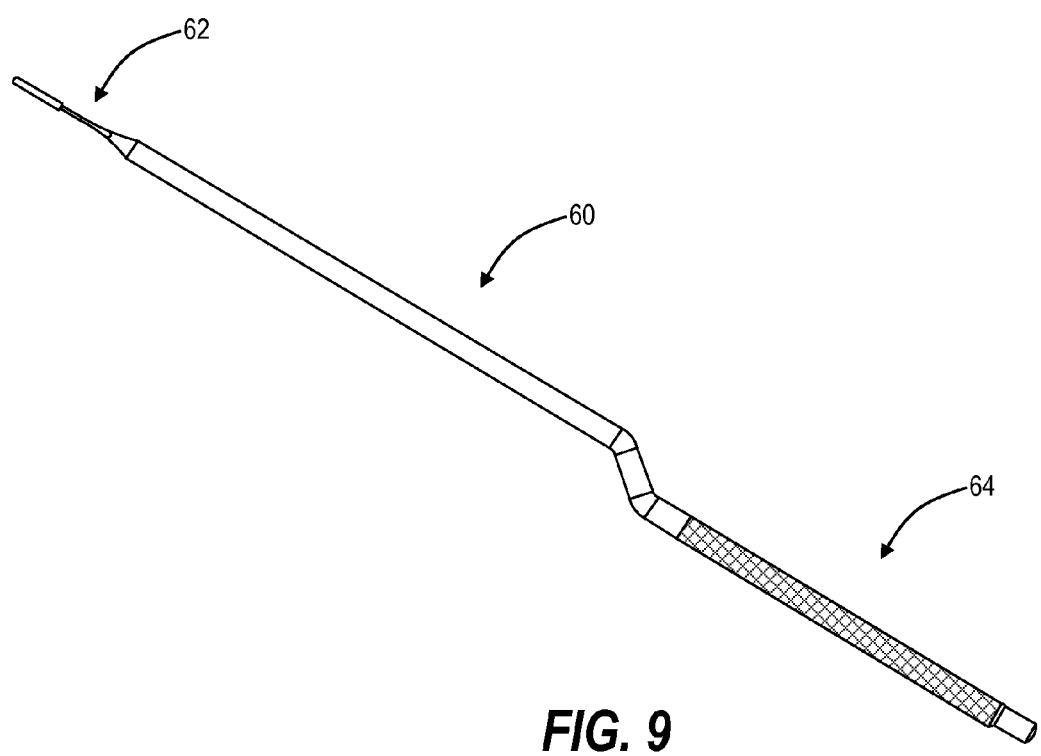
FIG. 9 is a planar diagram illustrating one exemplary embodiment of a flat rasp tool of the present invention, used in conjunction with the facet stabilization device of the present invention.
Figure 10:
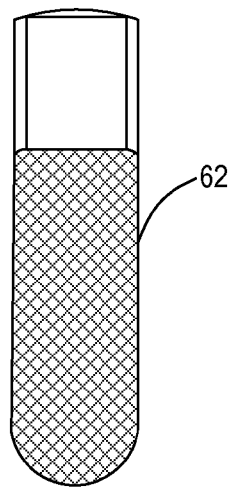
FIG. 10 is a planar diagram illustrating one exemplary embodiment of the friction head of the flat rasp tool of FIG. 9.
Figure 12:
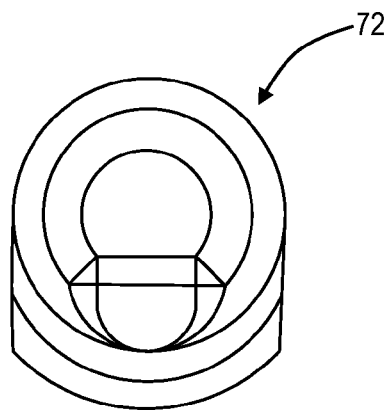
FIG. 12 is a planar diagram illustrating one exemplary embodiment of the friction head of the D-rasp tool of FIG. 11.
Figure 11:
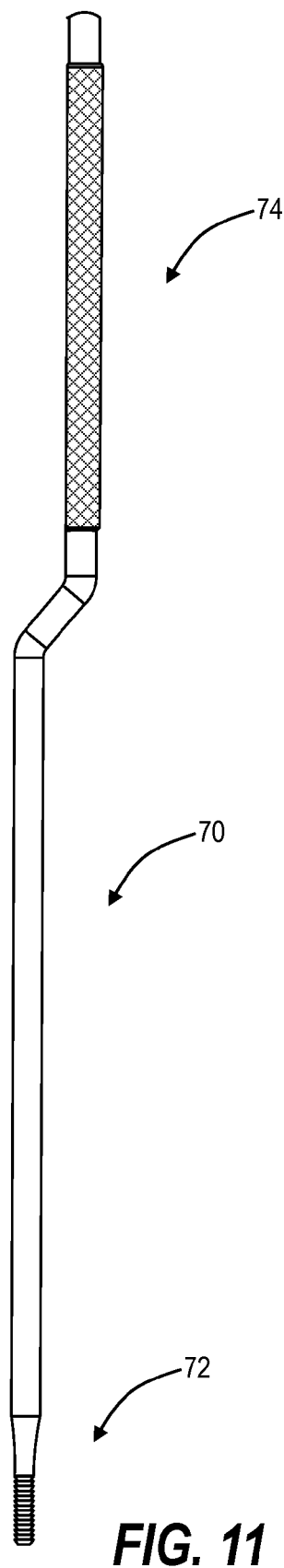
FIG. 11 is a planar diagram illustrating one exemplary embodiment of a D-rasp tool of the present invention, used in conjunction with the facet stabilization device of the present invention.

For example, FIG. 6 is a perspective diagram illustrating one exemplary embodiment of a dilator tube 40 of the present invention, used in conjunction with the facet stabilization device of the present invention. These dilator tubes 40 may come in a graduated range of sizes and be used to establish and maintain access to the facet joint 30 (FIGS. 2-5) of interest, as is well known to those of ordinary skill in the art. FIG. 7 is a perspective diagram illustrating one exemplary embodiment of a drill guide assembly 42 of the present invention, used in conjunction with the facet stabilization device of the present invention. This drill guide assembly 42 may be used in conjunction with the facet distraction instrument 10 (FIG. 1), taking the place of the associated cannulated drill portion 20 (FIG. 1), the dilator tubes 40 just described, or otherwise. Preferably, the drill guide assembly 42 includes a cannulated drill guide portion 44 and a handle portion 46 disposed at an angle and/or offset to the drill guide portion 44. Optionally, the cannulated drill guide portion 44 terminates in one or more friction structures 48 that are designed and positioned to engage a bony surface or the like. The cannulated drill guide portion 44 is sized and shaped to receive a drill assembly 50 (FIG. 8) or the like concentrically within it. Accordingly, the drill assembly includes a drill bit portion 52 or other cutting or rasping surface and a drive portion 54 that is configured to engage a drill or other driver handle. FIG. 9 is a planar diagram illustrating one exemplary embodiment of a flat rasp tool 60 of the present invention, used in conjunction with the facet stabilization device of the present invention. Preferably, the flat rasp tool 60 includes a friction head 62 and a handle portion 64 disposed at an angle and/or offset to the friction head 62. FIG. 10 is a planar diagram illustrating one exemplary embodiment of the friction head 62 of the flat rasp tool 60. FIG. 11 is a planar diagram illustrating one exemplary embodiment of a D-rasp tool 70 of the present invention, used in conjunction with the facet stabilization device of the present invention. Preferably, the D-rasp tool 60 includes a friction head 72 and a handle portion 74 disposed at an angle and/or offset to the friction head 72. FIG. 12 is a planar diagram illustrating one exemplary embodiment of the friction head 72 of the D-rasp tool 70. Again, any and all of these tools may be used in conjunction with the facet distraction instrument 10, the dilator tubes 40 described above, each other, or otherwise.

Figure 13:
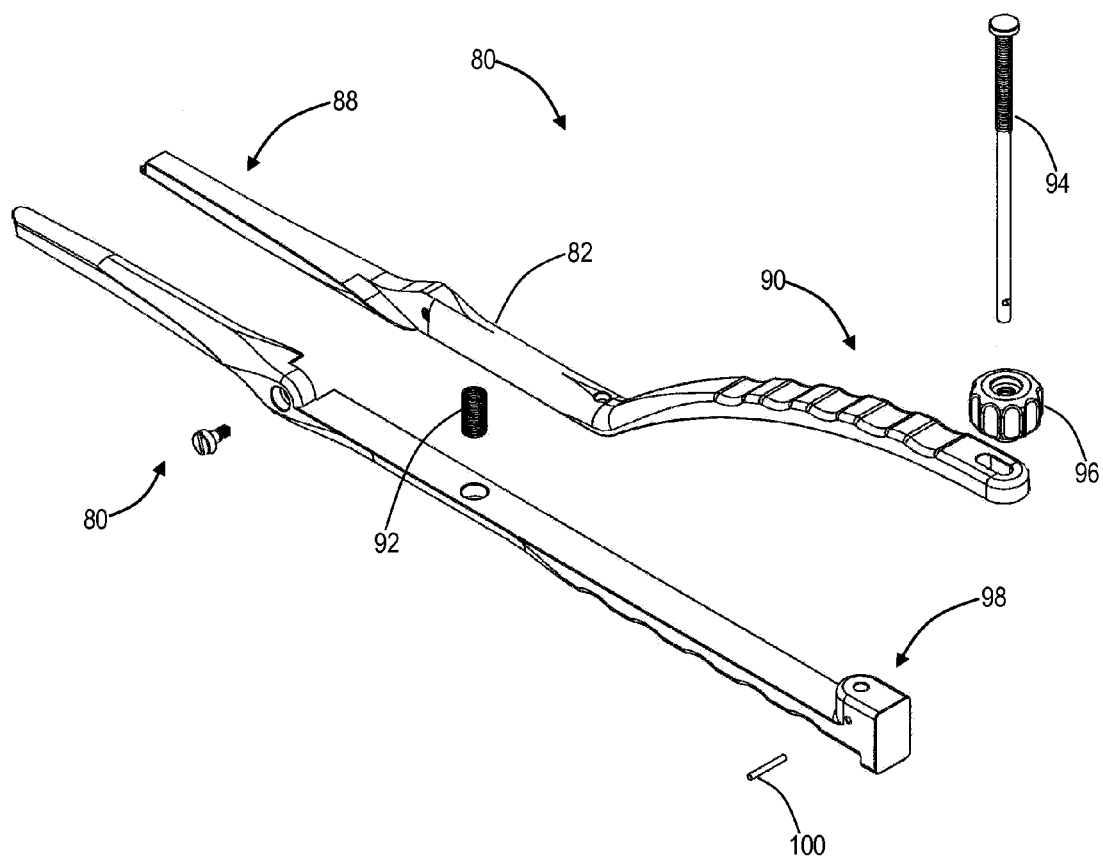
FIG. 13 is a disassembled perspective diagram illustrating one exemplary embodiment of an implant inserter of the present invention, used in conjunction with the facet stabilization device of the present invention.

FIG. 13 is a disassembled perspective diagram illustrating one exemplary embodiment of an implant inserter 80 of the present invention, used in conjunction with the facet stabilization device of the present invention. This implant inserter 80 may be used in conjunction with the facet distraction instrument 10 (FIG. 1), the dilator tubes 40 (FIG. 6) described above, or otherwise. The implant inserter 80 includes a first arm member 82 coupled to a second arm member 84 at a pivot point via a screw 86 or the like. Each arm member 82,84 includes a grasping portion 88 and a handle portion 90, such that the grasping portions 88 are deployed together or apart via actuation of the handle portions 90. Optionally, the handle portions 90 are biased apart, and the grasping portions 88 are biased together via a spring 92 or the like disposed between the arm members 82,84 adjacent to the pivot point. In the exemplary embodiment illustrated, the handle portions 90 are brought together or allowed to separate via the actuation of a partially threaded bolt 94 that is threaded through a thumb nut 96 and a hole in the handle portion 90 of the first arm member 82 and into a bore 98 associated with the handle portion 90 of the second arm member 84, where the threaded bolt 94 is secured with a pin 100 or the like.

Figure 14:
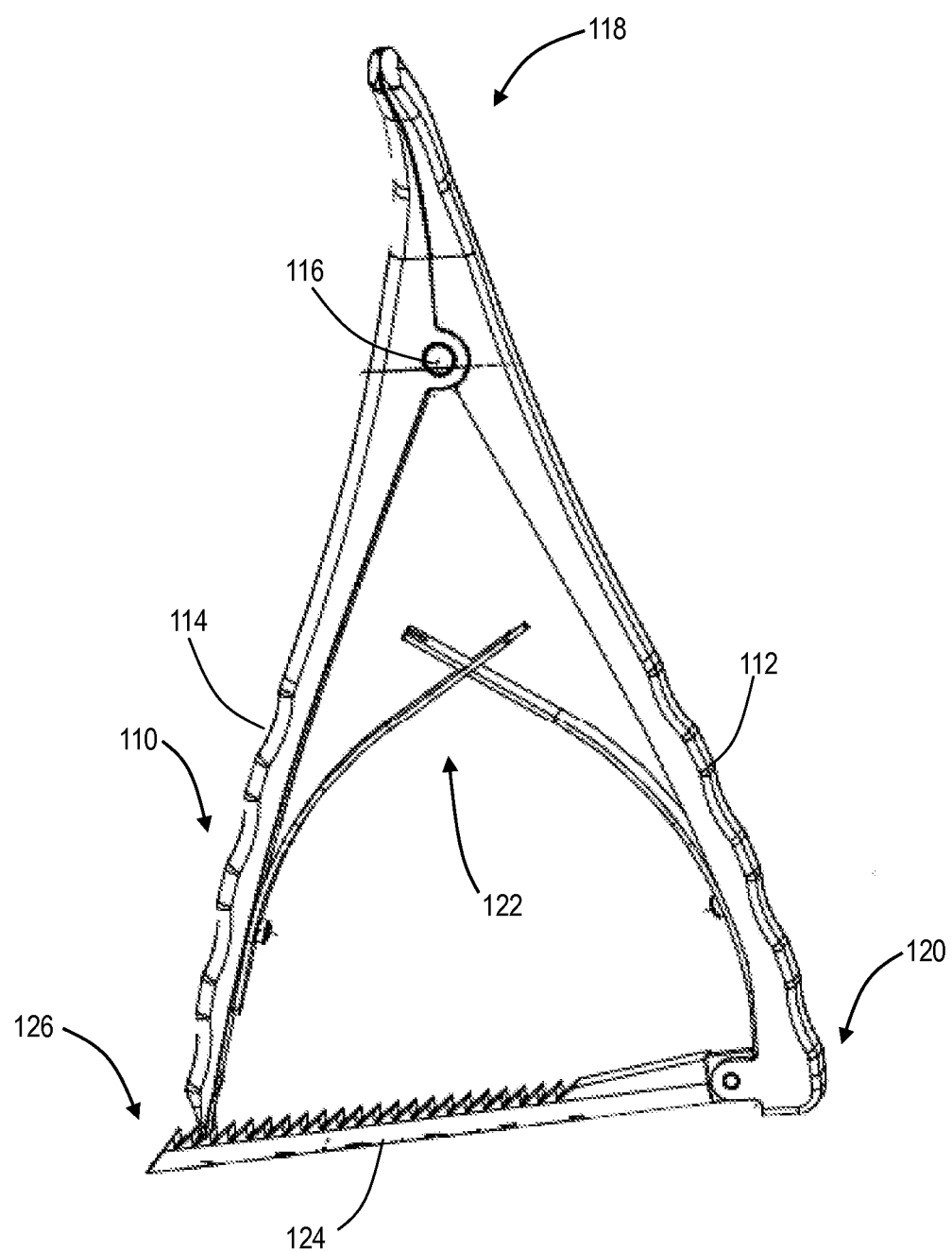
FIG. 14 is a perspective diagram illustrating one exemplary embodiment of a facet joint expander of the present invention, used in conjunction with the facet stabilization device of the present invention.

FIG. 14 is a perspective diagram illustrating one exemplary embodiment of a facet joint expander 110 of the present invention, used in conjunction with the facet stabilization device of the present invention. Again, this facet joint expander 110 may be used in conjunction with the facet distraction instrument 10 (FIG. 1), the dilator tubes 40 (FIG. 6) described above, or otherwise. The facet joint expander 110 includes a first arm member 112 coupled to a second arm member 114 at a pivot point via a screw 116 or the like. Each arm member 112,114 includes a grasping portion 118 and a handle portion 120, such that the grasping portions 118 are deployed together or apart via actuation of the handle portions 120. Optionally, the grasping portions 118 are substantially curved. Optionally, the handle portions 120 are biased apart, and the grasping portions 118 are biased together via a spring assembly 122 or the like disposed between the arm members 112,114 adjacent to the pivot point. In the exemplary embodiment illustrated, the handle portions 120 are brought together or allowed to separate via the actuation of a partially serrated member 124 that is pivotably coupled to the handle portion 120 of the first arm member 112 and engages a tooth structure 126 or other such edge associated with the handle portion 120 of the second arm member 114.

Figure 15:
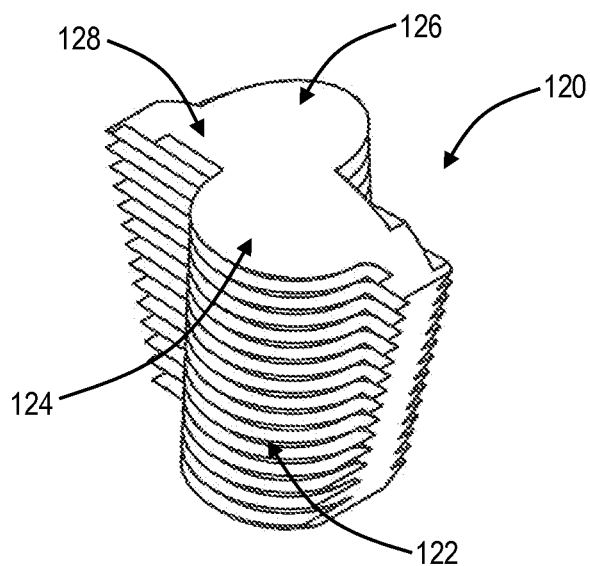
FIG. 15 is a perspective diagram illustrating one exemplary embodiment of a facet stabilization device, i.e. an allograft, of the present invention.
Figure 16:
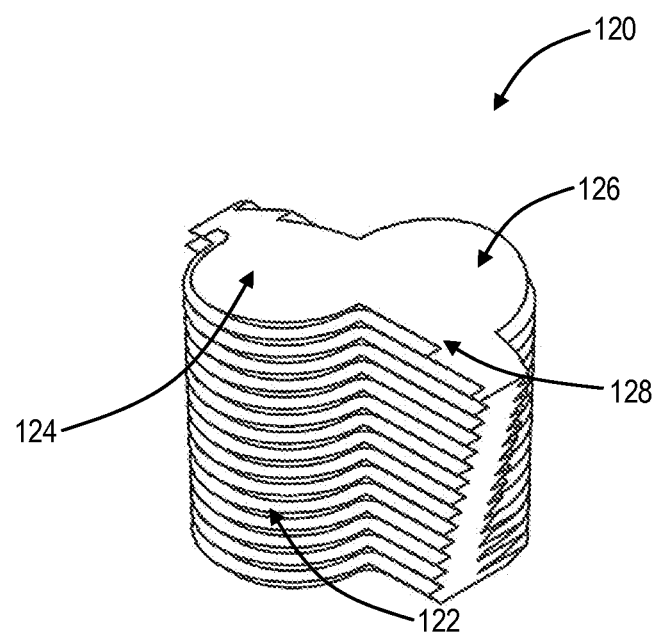
FIG. 16 is a perspective diagram illustrating another exemplary embodiment of a facet stabilization device, i.e. an allograft, of the present invention.

FIG. 15 is a perspective diagram illustrating one exemplary embodiment of a facet stabilization device 120, i.e. an allograft, of the present invention. In general, this facet stabilization device 120 is a partially conical or tapered structure (e.g. tapered from "top" to "bottom") that has a plurality of threads, concentric ridges, or other friction structures 122 on its outer surface, such that it will firmly engage the bony material of a corresponding hole or bore without backing out when driven into such a hole or bore. In this exemplary embodiment, the facet stabilization device 120 includes a first semicircular lobe 124 and a second semicircular lobe 126 that are offset and disposed about a generally rectangular center section 128 (or other suitable shape center section). It will be apparent to those of ordinary skill in the art that these lobes 124,126 may correspond to a hole or bore that is drilled in a facet joint 30 (FIGS. 2-5), the facets 32,34 (FIGS. 2-5) of which are then distracted apart, as described above. This facet stabilization device 120 may be disposed in the drilled and distracted "holes" in order to secure the facet joint 30 in its distracted state, for example. The facet stabilization device 120 may come in "right" or "left" side configurations (see also FIG. 16), a variety of shapes, and a variety of sizes, and may be made of any surgically implantable material, such as a metal, a polymeric material, a ceramic material, a bone graft material, etc.

In one exemplary embodiment, the facet stabilization device 120 is made of two or more materials with differing mechanical properties. A compressible, more compliant, material is used to house a more rigid material such that when a load is applied to the implant, the compressible material is reduced in dimension to reveal a portion of the more rigid material, with the more rigid material configured and sized to engage, attach to, or interfere with adjacent tissue or bone. For example, the compressible material may be mineralized cancellous bone, demineralized cancellous bone, demineralized cortical bone, etc. The more rigid material may be mineralized cancellous bone, mineralized cortical bone, demineralized cancellous bone, demineralized cortical bone, etc. At least one component may have properties that make it osteostimulative, osteoconductive, osteogenic, osteoinductive, or osteoinductive potential. These properties may be inherent or added prior to implantation by the use of cells or growth factors.

Figure 17:
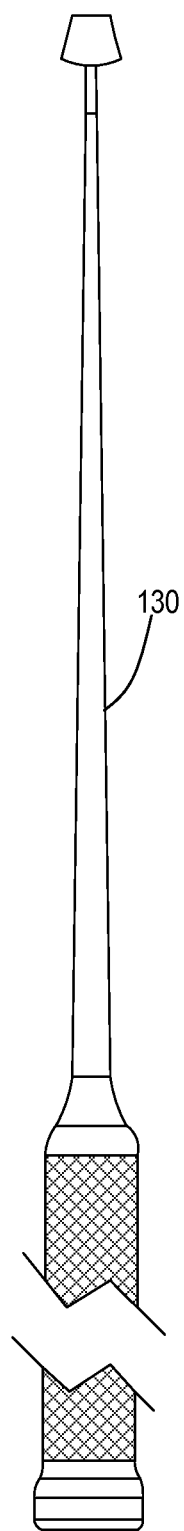
FIG. 17 is a planar diagram illustrating one exemplary embodiment of a trial facet stabilization device of the present invention, used to test the space available for placement of the facet stabilization device of the present invention.

FIG. 17 is a planar diagram illustrating one exemplary embodiment of a trial facet stabilization device 130 of the present invention, used to test the space available for placement of the facet stabilization device of the present invention.

Figure 18:
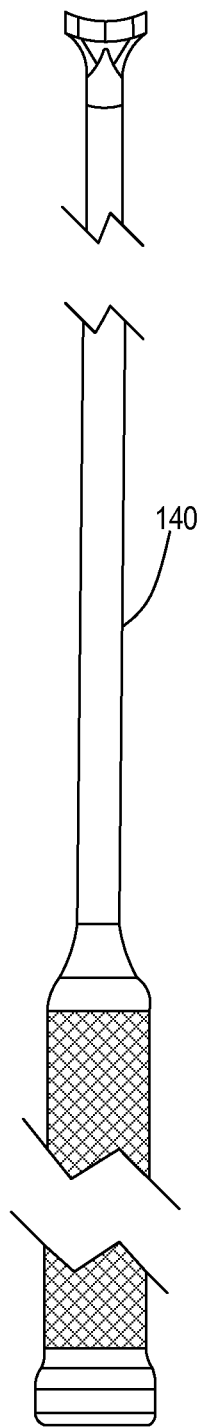
FIG. 18 is a planar diagram illustrating one exemplary embodiment of a tamp of the present invention, used to seat the facet stabilization device of the present invention.

FIG. 18 is a planar diagram illustrating one exemplary embodiment of a tamp 140 of the present invention, used to seat the facet stabilization device of the present invention.

Figure 19:
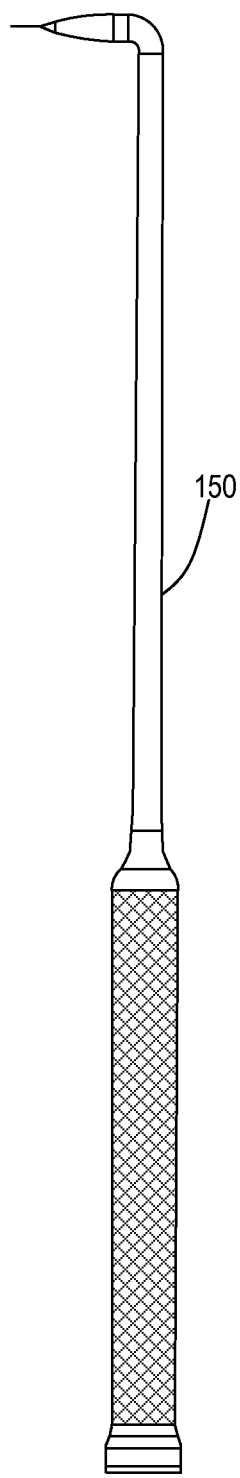
FIG. 19 is a planar diagram illustrating one exemplary embodiment of a ligament dilator of the present invention, used to create ligament access for placement of the facet stabilization device of the present invention.
Figure 20:
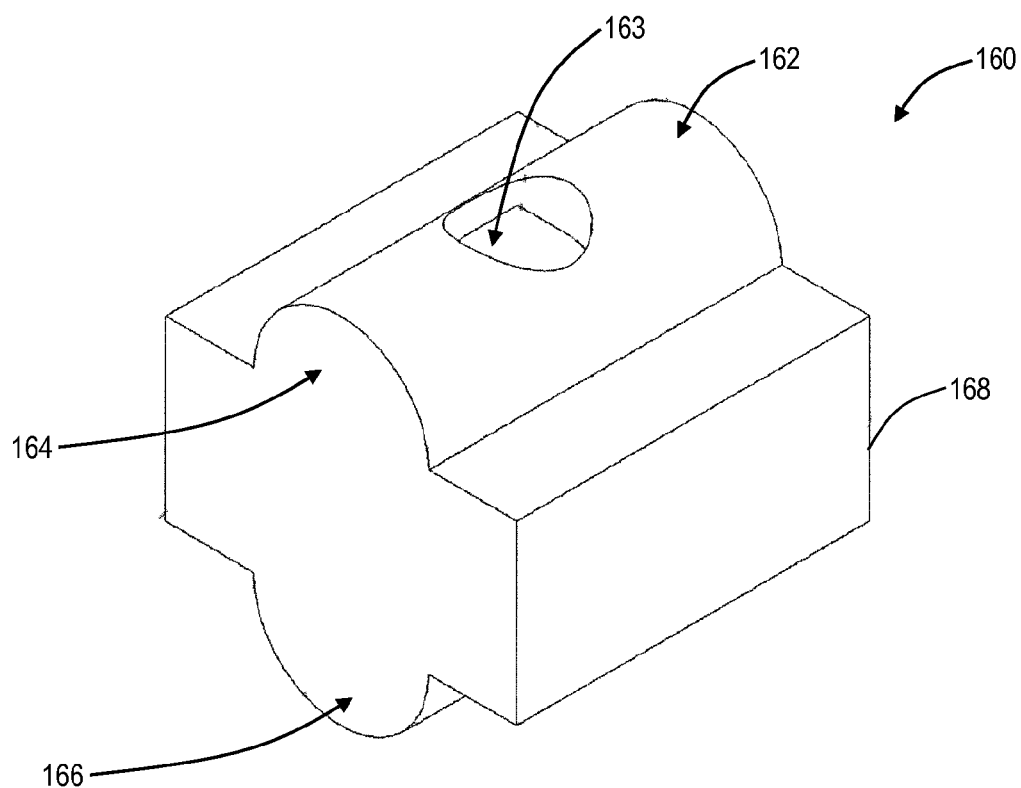
FIG. 20 is a perspective diagram illustrating another exemplary embodiment of the facet stabilization device of the present invention.
Figure 21:
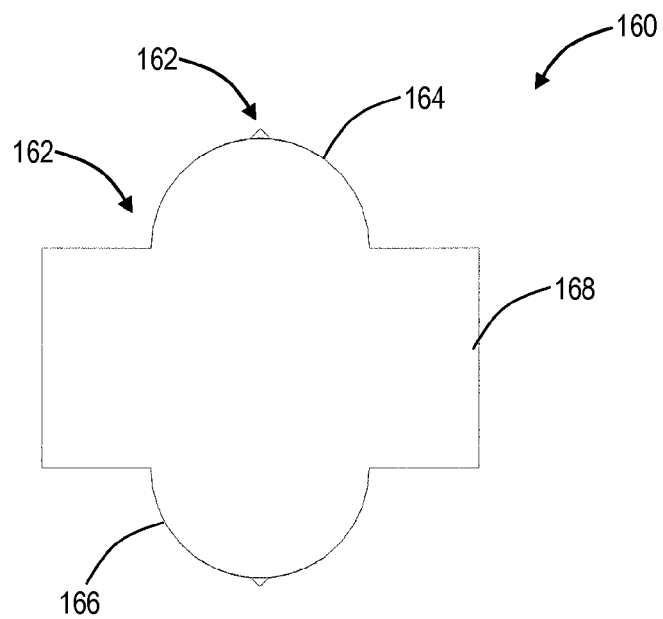
FIG. 21 is a planar diagram illustrating another exemplary embodiment of the facet stabilization device of the present invention.
Figure 22:
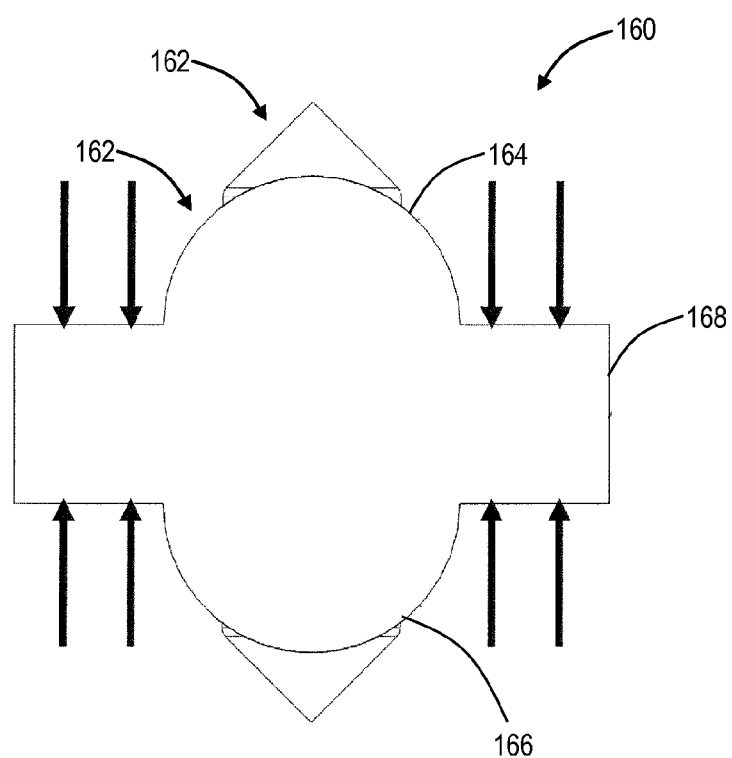
FIG. 22 is a planar diagram illustrating another exemplary embodiment of the facet stabilization device of the present invention.
Figure 23:
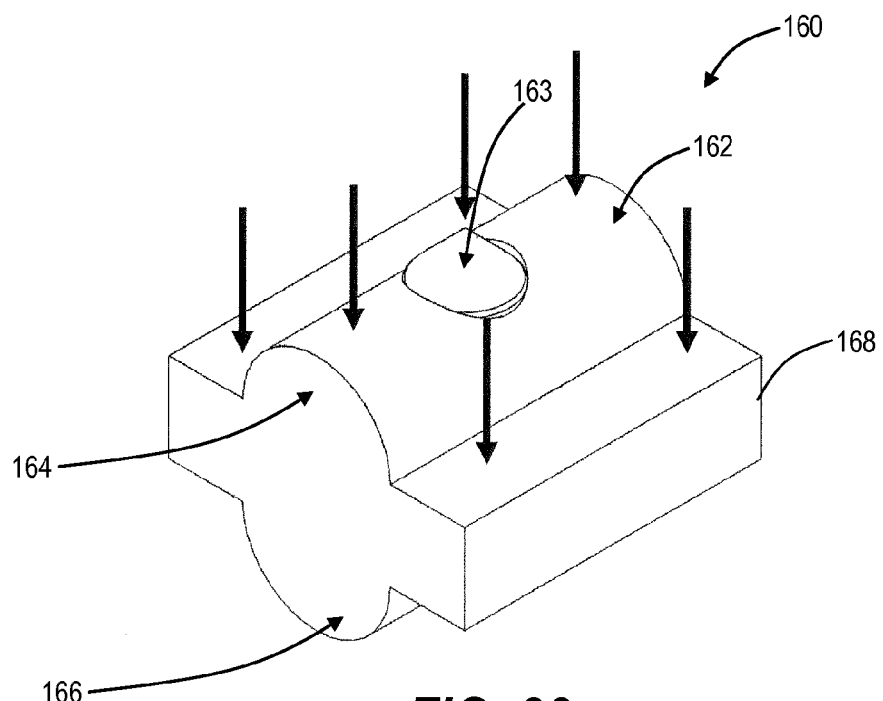
FIG. 23 is a perspective diagram illustrating another exemplary embodiment of the facet stabilization device of the present invention.

FIG. 19 is a planar diagram illustrating one exemplary embodiment of a ligament dilator 150 of the present invention, used to create ligament access for placement of the facet stabilization device of the present invention.

FIGS. 20-23 are perspective and planar diagrams illustrating another exemplary embodiment of a facet stabilization device 160, i.e. an allograft, of the present invention. In general, this facet stabilization device 160 is a prismatic structure that optionally has a plurality of threads, concentric ridges, or other friction structures (not illustrated) on its outer surface, such that it will firmly engage the bony material of a corresponding hole or bore without backing out when driven into such a hole or bore. In this exemplary embodiment, the facet stabilization device 160 includes a first semicircular lobe 164 and a second semicircular lobe 166 that are aligned and disposed about a generally rectangular center section 168 (or other suitable shape center section). It will be apparent to those of ordinary skill in the art that these lobes 164,166 may correspond to a hole or bore that is drilled in a facet joint 30 (FIGS. 2-5). The facet stabilization device 160 may come in a variety of shapes and a variety of sizes, and may be made of any surgically implantable material, such as a metal, a polymeric material, a ceramic material, a bone graft material, etc.

In one exemplary embodiment, the facet stabilization device 160 is made of two or more materials 162,163 with differing mechanical properties. A compressible, more compliant, material 162 is used to house a more rigid material 163 such that when a load is applied to the implant, the compressible material 162 is reduced in dimension to reveal a portion of the more rigid material 163, with the more rigid material 163 configured and sized to engage, attach to, or interfere with adjacent tissue or bone. For example, the compressible material 162 may be mineralized cancellous bone, demineralized cancellous bone, demineralized cortical bone, etc. The more rigid material 163 may be mineralized cancellous bone, mineralized cortical bone, demineralized cancellous bone, demineralized cortical bone, etc. At least one component may have properties that make it osteostimulative, osteoconductive, osteogenic, osteoinductive, or osteoinductive potential. These properties may be inherent or added prior to implantation by the use of cells or growth factors.

Figure 24:
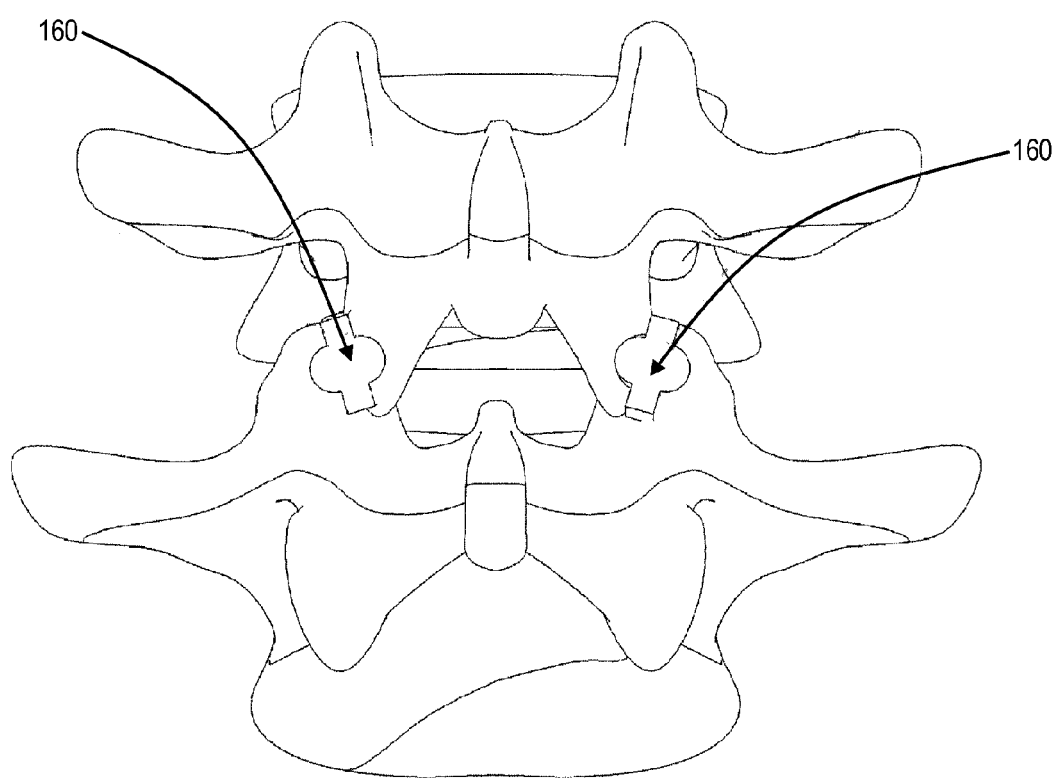
FIG. 24 is a schematic diagram illustrating one exemplary embodiment of the placement of the facet stabilization device of the present invention in the facet joints of the spine of a patient.

FIG. 24 is a schematic diagram illustrating one exemplary embodiment of the placement of the facet stabilization device 160 of the present invention in the facet joints 30 (FIGS. 2-5) of the spine of a patient.

Figure 25:
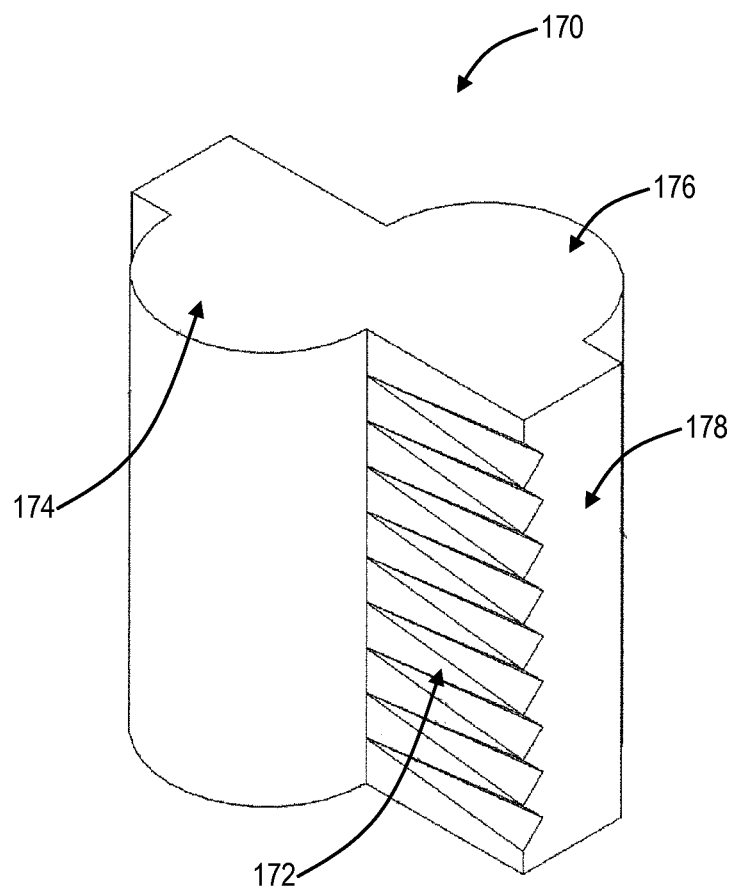
FIG. 25 is a perspective diagram illustrating a further exemplary embodiment of the facet stabilization device of the present invention.

FIG. 25 is a perspective diagram illustrating a further exemplary embodiment of a facet stabilization device 170, i.e. an allograft, of the present invention. In general, this facet stabilization device 170 is a prismatic structure that has a plurality of threads, concentric ridges, or other friction structures 172 on a portion of its outer surface, such that it will firmly engage the bony material of a corresponding hole or bore without backing out when driven into such a hole or bore. In this exemplary embodiment, the facet stabilization device 170 includes a first semicircular lobe 174 and a second semicircular lobe 176 that are offset and disposed about a generally rectangular center section 178 (or other suitable shape center section). It will be apparent to those of ordinary skill in the art that these lobes 174,176 may correspond to a hole or bore that is drilled in a facet joint 30 (FIGS. 2-5), the facets 32,34 (FIGS. 2-5) of which are then distracted apart, as described above. This facet stabilization device 170 may be disposed in the drilled and distracted "holes" in order to secure the facet joint 30 in its distracted state, for example. The facet stabilization device 120 may come in "right" or "left" side configurations, a variety of shapes, and a variety of sizes, and may be made of any surgically implantable material, such as a metal, a polymeric material, a ceramic material, a bone graft material, etc. In this exemplary embodiment, the facet implant comprises a rigid material with at least two opposing extensions to act on both the superior and inferior facets. These extensions help maintain spacing between the facets in the vertical plane increasing foraminal space and decompressing nerve roots. In accordance with one aspect of a preferred embodiment, the area adjacent to the extensions may be roughened by grooves, spikes, or other surface features to enhance friction and help resist expulsion of the implant. In accordance with another aspect of a preferred embodiment, the faces of the facet joint may be surgically prepared such that they are configured and dimensioned to engage the extensions found on the implant surface. In addition, the implant may be implanted and positioned while the foraminal space is distracted, maintaining vertical spacing after the conclusion of surgery.

Figure 26:
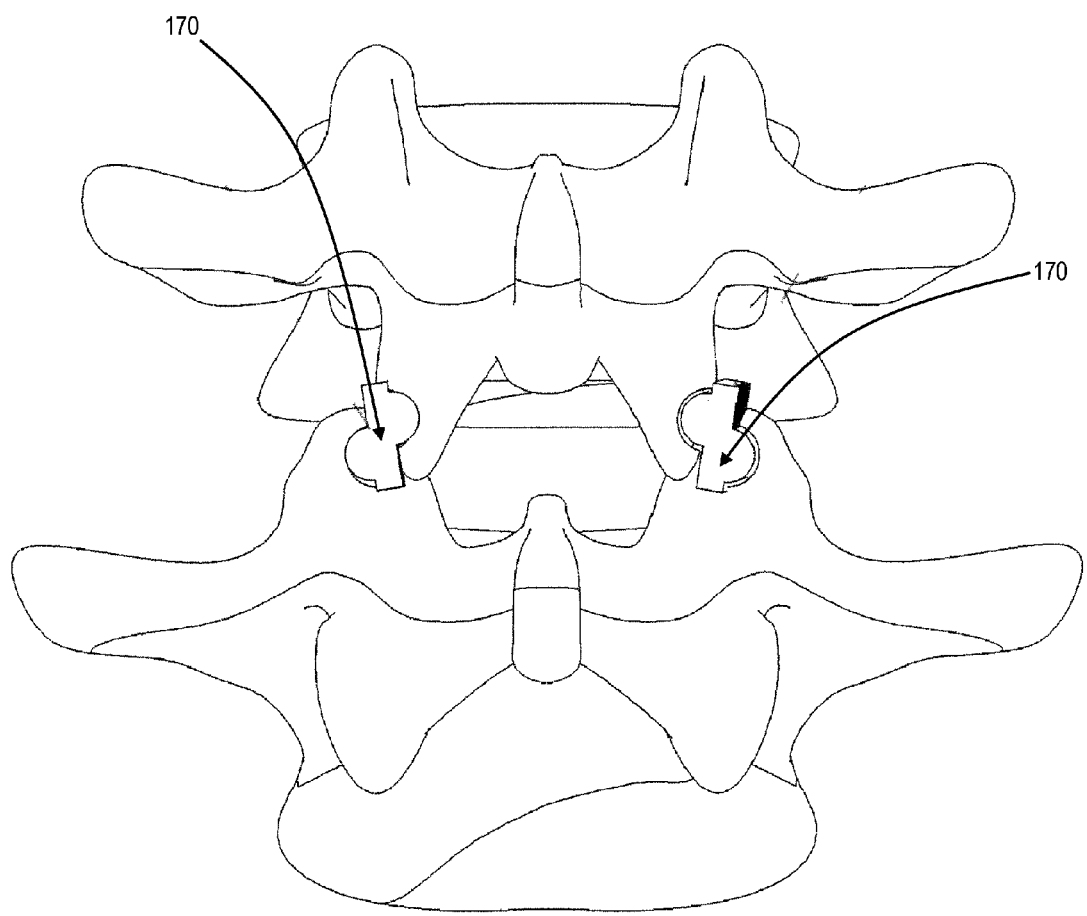
FIG. 26 is a schematic diagram illustrating another exemplary embodiment of the placement of the facet stabilization device of the present invention in the facet joints of the spine of a patient.

FIG. 26 is a schematic diagram illustrating another exemplary embodiment of the placement of the facet stabilization device 170 of the present invention in the facet joints 30 (FIGS. 2-5) of the spine of a patient.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A facet joint stabilization method, comprising:
   drilling a first hole in a facet joint of a spine of a patient, the facet joint comprising a first facet and a second facet;
   drilling a second hole in the facet joint, wherein the second hole is offset from the first hole;
   positioning a facet joint stabilization device in the first and second holes, the facet joint stabilization device comprising:
   an elongated body section having a length extending along an axis when viewed from a top surface of the facet joint stabilization device and having a width when viewed from the top surface extending at least substantially perpendicular to the length, wherein the length is greater than the width;
   a substantially solid first lobe section protruding outwardly from the body section; and
   a substantially solid second lobe section protruding outwardly from the body section, wherein the facet joint stabilization device is positioned in the first and second holes such that the substantially solid first lobe section engages bone material from the first facet and such that the substantially solid second lobe section engages bone material from the second facet, wherein the first lobe section and the second lobe section are offset with respect to one another in relation to the body section such that the first lobe section is positioned along a different portion of the length of the body section on a first side of the body section opposite from a second side of the body section on which the second lobe section is positioned, wherein the first lobe section is not symmetrical with respect to the second lobe section about the axis, and wherein the facet joint stabilization device is positioned in the first and second holes such that the first lobe section is positioned in the first hole and the second lobe section is positioned in the second hole.

2. The facet joint stabilization method of claim 1, wherein one or more of the body section, the first lobe section, and the second lobe section comprise an outer material and an inner material, wherein the outer material is more compressible than the inner material.

3. The facet joint stabilization method of claim 2, wherein a portion of the inner material protrudes through and beyond a surface of the outer material when the outer material is compressed in a facet joint space.

4. The facet joint stabilization method of claim 1, further comprising:
   drilling a third hole in a second facet joint of a spine of a patient, the second facet joint comprising a first facet and a second facet, and wherein the second facet joint is positioned on the opposite side of the patient's spine relative to the facet joint;
   drilling a fourth hole in the second facet joint, wherein the fourth hole is offset from the third hole;
   positioning a second facet joint stabilization device in the third and fourth holes, the second facet joint stabilization device comprising:
   a body section;
   a substantially solid first lobe section protruding outwardly from the body section; and
   a substantially solid second lobe section protruding outwardly from the body section, wherein the second facet joint stabilization device is positioned in the second hole such that the substantially solid first lobe section engages bone material from the first facet of the second facet joint and such that the substantially solid second lobe section engages bone material from the second facet of the second facet joint, and wherein the second facet joint stabilization device differs from the first facet joint stabilization device so as to account for anatomical differences between the facet joint and the second facet joint, wherein the first lobe section and the second lobe section of the second facet joint stabilization device are offset with respect to one another in relation to the body section such that the first lobe section is positioned along a different portion of a length of the body section opposite from the second lobe section, and wherein the second facet joint stabilization device is positioned in the third and fourth holes such that the first lobe section is positioned in the third hole and the second lobe section is positioned in the fourth hole.

5. The facet joint stabilization method of claim 4, wherein:

the position of the first lobe section of the first facet joint stabilization device relative to the second lobe section of the first facet joint stabilization device differs from the position of the first lobe section of the second facet joint stabilization device relative to the second lobe section of the second facet joint stabilization device such that the first facet joint stabilization device is configured for use in connection with a facet joint on the left side of the patient's spinal column and the second facet joint stabilization device is configured for use in connection with a facet joint on the right side of the patient's spinal column.

6. The facet joint stabilization method of claim 1, wherein the body section has a substantially rectangular shape, and wherein each of the first lobe section and the second lobe section has a substantially semicircular shape.

7. The facet joint stabilization method of claim 1, wherein the facet joint stabilization device comprises at least one of a prismatic structure and a tapering structure.

8. The facet joint stabilization method of claim 1, wherein the first lobe section and the second lobe section are in alignment with respect to one another in relation to the body section.

9. The facet joint stabilization method of claim 1, wherein the first lobe section and the second lobe section are offset with respect to one another in relation to the body section.

10. The facet joint stabilization method of claim 1, wherein one or more of the body section, the first lobe section, and the second lobe section comprise one or more friction structures on an outer surface thereof, and wherein the facet joint stabilization device is positioned within the first and second holes such that the one or more friction surfaces firmly engage bone material defining a hole in the facet joint.

11. The facet joint stabilization method of claim 1, wherein the facet joint stabilization device comprises one or more bone materials.

12. The facet joint stabilization method of claim 1, further comprising distracting the facet joint prior to positioning the facet joint stabilization device in the first and second holes formed in the facet joint of the spine of the patient.

* * * * *